(12) United States Patent
Juo et al.

(10) Patent No.: US 10,179,913 B2
(45) Date of Patent: Jan. 15, 2019

(54) MICRORNA-328 ANTI-SENSE COMPOSITION AND THERAPEUTIC USE

(71) Applicant: KAOHSIUNG MEDICAL UNIVERSITY, Kaohsiung (TW)

(72) Inventors: Suh-Hang H. Juo, Kaohsiung (TW); Edward Hsi, Kaohsiung (TW); Chung-Ling Liang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 15/747,153

(22) PCT Filed: Jul. 28, 2016

(86) PCT No.: PCT/CN2016/092060
§ 371 (c)(1),
(2) Date: Jan. 24, 2018

(87) PCT Pub. No.: WO2017/032201
PCT Pub. Date: Mar. 2, 2017

(65) Prior Publication Data
US 2018/0216109 A1      Aug. 2, 2018

Related U.S. Application Data

(60) Provisional application No. 62/210,340, filed on Aug. 26, 2015.

(51) Int. Cl.
| | | |
|---|---|---|
| *A61K 48/00* | (2006.01) |
| *C07H 21/02* | (2006.01) |
| *C07H 21/04* | (2006.01) |
| *C12N 15/113* | (2010.01) |
| *A61K 31/711* | (2006.01) |
| *A61K 31/712* | (2006.01) |
| *A61P 27/10* | (2006.01) |

(52) U.S. Cl.
CPC .......... *C12N 15/113* (2013.01); *A61K 31/711* (2013.01); *A61K 31/712* (2013.01); *A61P 27/10* (2018.01); *C12N 2310/11* (2013.01); *C12N 2310/113* (2013.01); *C12N 2310/141* (2013.01); *C12N 2310/315* (2013.01); *C12N 2310/3231* (2013.01); *C12N 2310/346* (2013.01)

(58) Field of Classification Search
CPC .... C12N 15/111; C12N 15/113; A61K 31/713
See application file for complete search history.

(56) References Cited

FOREIGN PATENT DOCUMENTS

WO     WO 2008/131191 A2 * 10/2008 ........... A61K 31/713

OTHER PUBLICATIONS

Seth et al. (Molecular Therapy—Nucleic Acids, 2012, 1, e47, pp. 1-8).*
Chen et al. (Accession JP757699.1, Nov. 2011) (SCORE search result #7 in the file titled "20180718_122354_us-15-747-153-3.rge").*

* cited by examiner

*Primary Examiner* — Amy H Bowman
(74) *Attorney, Agent, or Firm* — Hannah M. Tien

(57) ABSTRACT

The present invention is directed to anti-sense microRNA-328 in a form of oligodeoxyribonucleotides, or locked nucleic acid (LNA)-modified, and phosphorothioated (PS) bond-modified oligonucleotides. The present invention is also directed to a pharmaceutical composition comprising the anti-sense microRNA-328 composition and a pharmaceutically acceptable carrier. The present invention is further directed to a method for preventing or treating myopia by administering to a subject the anti-sense microRNA-328 composition. A preferred route of administration is topical administration to the eyes.

8 Claims, 5 Drawing Sheets

Specification includes a Sequence Listing.

MICRORNA-328 ANTI-SENSE COMPOSITION AND THERAPEUTIC USE

CROSS-REFERENCES TO RELATED APPLICATIONS

This patent application is the U.S. National Stage Application of PCT/CN2016/092060 filed Jul. 28, 2016 and claims the benefit of priority from the U.S. Provisional Application Ser. No. 62/210,340 filed on Aug. 26, 2015, the contents of each of which is incorporated herein by reference in their entirety. This application also contains a Sequence Listing in computer readable form which is incorporated herein by reference.

TECHNICAL FIELD

The present invention relates to anti-sense microRNA-328 in a form of oligodeoxyribonucleotide or locked nucleic acid (LNA)-modified and phosphorothioate bond-modified oligonucleotides, and their therapeutic use in treating ocular diseases such as myopia.

BACKGROUND OF THE INVENTION

Myopia causes the eye to elongate, which in turn stretches and thins the retina and the sclera of the eye. Accordingly a myopic eye has a longer axial length than the normal eye. Noticeably, the axial length can vary among individuals. In animal studies, one eye is induced to myopia and the other eye is used as the control. The difference of axial length between the induced myopic eye and the control eye can be used to indicate the severity of myopia. In addition, the change of difference of axial length can also be used as a readout to assess the therapeutic effect for anti-myopic treatment. The elongation of eyeball is considered the major underlying mechanism to cause myopia complications such as retinal detachment, macular degeneration. That also explains why the correction of refraction without preventing axial length elongation (such as eyeglasses) cannot prevent myopia complications.

The paired box 6 (PAX6) gene belongs to a highly conserved family of transcription factors containing the paired and homeobox DNA-binding domains. PAX6 is involved in the development of the central nervous system and the eye. It plays significant roles during the induction of lens and retina differentiation, and has been considered the master gene in eye development. In humans, mutations in PAX6 are associated with a variety of human ocular diseases including aniridia, foveal hypoplasia, presenile cataract, and aniridia-related keratopathy (reviewed by Tsonis and Fuentes). In addition to the biological plausibility, a genome-wide linkage study revealed a strong linkage of refractive error to the PAX6 locus. Accordingly, PAX6, has been proposed as a candidate gene for the development of myopia. A low level of PAX6 may be a risk factor for myopia.

MicroRNAs (miRNAs) are noncoding, single-stranded RNA molecules of about 21-23 nucleotides in length. In animals, a mature miRNA is complementary to the 3' untranslated region (UTR) of one or more messenger RNAs (mRNAs). The annealing of a miRNA to its target mRNA causes an inhibition of protein translation, and/or cleavage of the mRNA. miRNAs can regulate cell growth, differentiation, and apoptosis.

Chen et al (Invest. Ophthalmol. Vis. Sci., 53:2732-2739, 2012) report that microRNA-328 (miR-328) may influence myopia development by mediating the PAX6 gene.

DETAILED DESCRIPTION OF THE INVENTION

Definition

Figure 1:
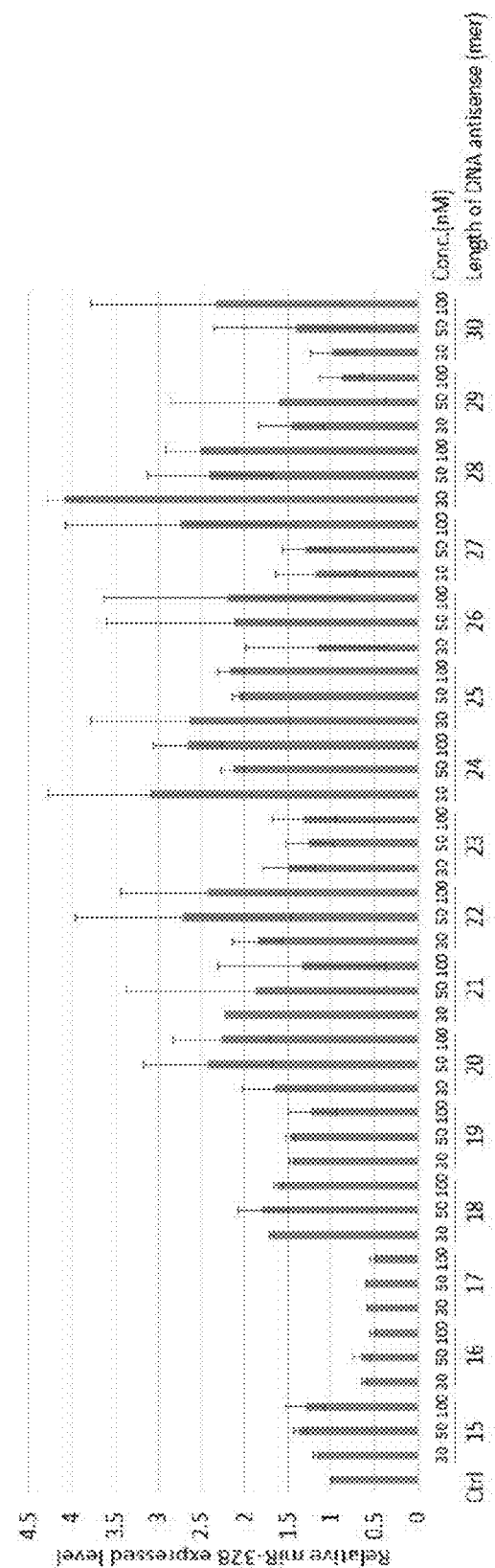
FIG. 1 shows relative miR-328 expressed levels in RPE cells after transfection with miR-328 anti-sense DNA (15mer-30mer) and control. Mean and standard deviation are shown (n=3).

A "locked nucleic acid" (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired.

An "oligodeoxyribonucleotide", as used herein, refer to a deoxyribonucleic acid (DNA) having 5-50 bases, preferably 10-30 bases, or 15-30 bases long. The DNA is optionally modified on the bases or on the phosphodiester bond.

An "oligoribonucleotide", as used herein, refer to a ribonucleic acid (RNA) having 5-50 bases, preferably 10-30 bases, or 15-30 bases long. The RNA is optionally modified.

An "oligonucleotide", as used herein, refer to an oligodeoxyribonucleotide, an oligoribonucleotide, or a hybrid thereof.

"Phosphorothioates" are a variant of normal DNA in which at least one of the non-bridging oxygens of the phosphodiester bonds is replaced by a sulfur. The sulfurization of the internucleotide bond dramatically reduces the action of endonucleases and exonucleases. Inclusion of phosphorothioate (PS) bonds increases oligonucleotide half-life in human serum; however, the introduction of PS bonds may lower the binding affinity of the oligonucleotides and may cause cytotoxicity.

The present invention is directed to oligonucleotide sequences that are anti-sense to miR-328. In one embodiment, the oligonucleotides are oligodeoxyribonucleotides that have specific lengths. In another embodiment, the oligonucleotides have LNA modifications and phosphorthioate modifications. The oligonucleotides of the present invention are useful to prevent or to treat ocular diseases such as myopia.

Human mature miR-328 has the sequence of CUGGCC-CUCUCUGCCUUCCGU (SEQ ID NO: 1).

In a first aspect of the invention, the inventors have designed anti-sense miR-328 oligodeoxyribonucleotides (15-22 mer in length) according to mature human miR-328, and designed anti-sense miR-328 oligodeoxyribonucleotides (23-30 mer in length) according to premature human miR-328 sequences. The inventors then obtained the miRNA-328 anti-sense DNAs having 15-30 bases (15-30mer) and tested their activities. The sequences of DNA 15mer-30mer are shown in Table 1.

TABLE 1

Antisense DNA sequence

| DNA Antisense | Sequence | SEQ ID NO: |
|---|---|---|
| DNA 30 mer | 5'-ACGGAAGGGCAGAGAGGGCCAGGGGCTGTA-3' | 17 |
| DNA 29 mer | 5'-ACGGAAGGGCAGAGAGGGCCAGGGGCTGT-3' | 16 |
| DNA 28 mer | 5'-ACGGAAGGGCAGAGAGGGCCAGGGGCTG-3' | 15 |
| DNA 27 mer | 5'-ACGGAAGGGCAGAGAGGGCCAGGGGCT-3' | 14 |
| DNA 26 mer | 5'-ACGGAAGGGCAGAGAGGGCCAGGGGC-3' | 13 |
| DNA 25 mer | 5'-ACGGAAGGGCAGAGAGGGCCAGGGG-3' | 12 |
| DNA 24 mer | 5'-ACGGAAGGGCAGAGAGGGCCAGGG-3' | 11 |
| DNA 23 mer | 5'-ACGGAAGGGCAGAGAGGGCCAGG-3' | 10 |
| DNA 22 mer | 5'-ACGGAAGGGCAGAGAGGGCCAG-3' | 9 |
| DNA 21 mer | 5'-ACGGAAGGGCAGAGAGGGCCA-3' | 8 |
| DNA 20 mer | 5'-CGGAAGGGCAGAGAGGGCCA-3' | 7 |
| DNA 19 mer | 5'-GGAAGGGCAGAGAGGGCCA-3' | 6 |
| DNA 18 mer | 5'-GAAGGGCAGAGAGGGCCA-3' | 5 |
| DNA 17 mer | 5'-AAGGGCAGAGAGGGCCA-3' | 4 |
| DNA 16 mer | 5'-AGGGCAGAGAGGGCCA-3' | 3 |
| DNA 15 mer | 5'-GGGCAGAGAGGGCCA-3' | 2 |

The inventors have discovered that out of the 16 antisense DNAs tested, only 16mer and 17mer inhibited miR-328 expression in vitro. Surprisingly, the anti-sense DNAs (15mer and 18-30mers) did not show any activity for inhibiting miR-328 expression in vitro. The 16mer and 17mer were safe in animal studies, and they exhibited an activity for treating myopia by decreasing an average axial length in the treated mice.

The present invention is directed to DNA 16mer, 5'-AGGGCAGAGAGGGCCA-3' (SEQ ID NO: 3) and DNA 17mer, 5'-AAGGGCAGAGAGGGCCA-3' (SEQ ID NO: 4).

In a second aspect of the invention, the inventors have designed LNA-modified, and phosphorothioate (PS) bond-modified antisense oligonucleotides, ranging from 17 to 22 mers according to mature human miR-328 sequence and gapmer principle (Kurreck et al, Nucleic Acids Res., 30: 1911-1918, 2002). The 15 and 16 mers of LNA-modified antisense oligonucleotides are not included, because the 5'-end terminal sequences of 15 and 16 mers show consecutive 3 G's and the self-complementary pattern, which can cause the oligonucleotide to form dimers. The inventors then obtained miRNA-328 anti-sense LNA modified oligonucleotides having 17-22 bases and tested their activities. The sequences of anti-sense miR-328 oligonucleotides that are LNA-modified and PS bond-modified are shown in Table 2. Their respective non-modified, native DNA sequences are shown in the computer-readable format of sequence listing as SEQ ID NOs: 18-23.

TABLE 2

LNA modified, and PS bond modifed Antisense oligonucleotide sequence

| Antisense | Sequence (LNA-modified and PS bond-modified) | SEQ ID NO^ (non-modified version) |
|---|---|---|
| 401 (22 mer) | 5'-+A*+C*+G*+G*A*A*G*G*G*C*A*G*A*G*A*G*G*G*+C*+C*+A*+G-3' | 23 |
| 402 (21 mer) | 5'-+A*+C*+G*+G*A*A*G*G*G*C*A*G*A*G*A*G*G*G*+G*+C*+C*+A-3' | 22 |
| 403 (20 mer) | 5'-+C*+G*+G*+A*A*G*G*G*C*A*G*A*G*A*G*G*+G*+C*+C*+A-3' | 21 |
| 404 (19 mer) | 5'-+G*+G*+A*+A*G*G*G*C*A*G*A*G*A*G*G*+G*+C*+C*+A-3' | 20 |
| 405 (18 mer) | 5'-+G*+A*+A*+G*G*G*C*A*G*A*G*A*G*+G*+G*+C*+C*+A-3' | 19 |
| 406 (17 mer) | 5'-+A*+A*+G*+G*G*C*A*G*A*G*A*G*+G*+G*+C*+C*+A-3' | 18 |

+: indicates Locked nucleic acid (LNA) modification;
*: indicates phosphodiester bonds were replaced by phosphorothioate bonds.
^indicates that SEQ ID NOs: 18-23 are the sequences of native (unmodified) oligonucleotides of their respective LNA-modified and PS-modified counterparts shown with "+" and "*" in the table.

In Table 2, every phosphodiester bond of the DNA sequences is modified to a phosphorothioate bond (PS). In Table 2, the central core of each DNA sequence is flanked by four LNA-modified nucleotides at both 5' and 3' ends.

The inventors have discovered that out of the 6 anti-sense LNA/PS bond modified oligonucleotides tested, only 403, 404, and 405 inhibited miR-328 expression in vitro. Other anti-sense LNA/PS bond modified DNAs did not show any activity for inhibition miR-328 expression in vitro. In addition to the in vitro activity, 403 exhibited an activity for treating myopia by decreasing an average axial length in the treated mice.

The present invention is directed to anti-sense LNA/PS bond modified oligonucleotides 403, 404, 405; with 403 being preferred.

The miRNA-328 antisense compositions of the present invention have good hybridization activity toward miRNA-328, have good solubility in water, and are stable (resistant to exonucleases).

PAX6, FMOD and COL1A1 are important genes in myopia pathogenesis and they are direct target genes of miR-328. These genes have been shown to play a role in myopia development. The miRNA-328 antisense compositions of the present invention increased the expression levels of PAX6, FMOD and COL1A1 in vitro.

The miRNA-328 antisense compositions of the present invention are useful in preventing or treating ocular diseases. In particular, the miRNA-328 antisense compositions of the present invention are useful in preventing or treating myopia.

The present invention is directed to a pharmaceutical composition comprising miRNA-328 anti-sense oligonucleotides of the present invention and a pharmaceutically acceptable carrier. A preferred form for treating myopia is a topical solution or a topical ointment.

A topical solution containing anti-sense miRNA-328 can contain a physiologically compatible vehicle, as those skilled in the ophthalmic art can select using conventional criteria. The ophthalmic vehicles include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

The formulation optionally includes a preservative, such as benzalkonium chloride and other inactive ingredients such as EDTA. However, for chronic (over two weeks) use, preferred formulations are those without any preservatives due to the potential for damage to the corneal epithelium that may result from long term, frequent exposure to preservatives such as benzalkonium chloride. The formulations without preservatives are prepared in a unit dose and stored in a single-use container.

The pH of the formulation is adjusted by adding any physiologically and ophthamologically acceptable pH adjusting acids, bases or buffers to within the range of about 5 to 7.5, preferably 6 to 7. Examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethyl-amino-methane), and the like. Salts and buffers include citrate/dextrose, sodium bicarbonate, ammonium chloride and mixtures of the aforementioned acids and bases.

The osmotic pressure of the aqueous ophthalmic composition is generally from about 200 to about 400 milliosmolar (mOsM), more preferably from 260 to 340 mOsM. The osmotic pressure can be adjusted by using appropriate amounts of physiologically and ophthamologically acceptable ionic or non-ionic agents. Sodium chloride is a preferred ionic agent, and the amount of sodium chloride ranges from about 0.01% to about 1% (w/v), and preferably from about 0.05% to about 0.45% (w/v). Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can be used in addition to or instead of sodium chloride to achieve osmolality within the above-stated range. Further, non-ionic agents such as mannitol, dextrose, sorbitol, glucose and the like can also be used to adjust the osmolality.

MiRNA-328 anti-sense oligonucleotides of the present invention can be administered to the eyes of a patient by any suitable means, but are preferably administered in the form of drops, spray, gel, or ointment. In one embodiment, the oligonucleotide is in the form of drops, and is dropped onto the ocular surface. In another embodiment, the oligonucleotide is contained within a swab or sponge which can be applied to the ocular surface. In another embodiment, the oligonucleotide is contained within a liquid spray or ointment which can be applied to the ocular surface. In another embodiment, the oligonucleotide is injected directly into the lacrimal tissues or onto the eye surface. Alternatively, the oligonucleotide can be applied to the eye via liposomes. Further, the oligonucleotide can be infused into the tear film via a pump-catheter system. As an additional embodiment, the oligonucleotide can be contained within, carried by, or attached to contact lenses or other compatible controlled release materials, which are placed on the eye.

The concentration of the oligonucleotide included in a topical solution is an amount sufficient to prevent and/or to treat myopia. The oligonucleotide concentration is generally in the range of about 30 nM-2.5 mM, preferably about 100 nM-10 µM, about 1 µM-100 µM, or about 15 µM-1.5 mM. "About", as used herein, refers to ±10% of recited value.

The present invention is further directed to a method for preventing or treating myopia in a subject. The method comprises the step of administering to a subject in need thereof an effective amount of the anti-sense microRNA-328 oligonucleotide composition of the present invention. Topical route of administration is preferred. "An effective amount", refers to an amount that is effective to prevent or to treat myopia, i.e., to prevent the axial length in the eye from increasing, or to reduce the axial length in the myopic eye.

The daily dose to treat or prevent myopia can be divided among one or several unit dose administrations. The daily dose, for example, can range from one drop (about 30-50 µl), one to four times a day, depending upon the age and condition of the subject. One regimen for miR-328 anti-sense DNA composition is one drop of the topical solution, 1 to 2 times a day. Alternatively, the topical solution can be administered one time per week.

When treating or preventing myopia, the present method can be combined with other methods known to a person skilled in the art.

The present invention also provides use of a deoxyribonucleotide sequence according to the present invention for the manufacture of a medication or pharmaceutical composition for preventing or treating myopia. In a preferred embodiment, the medication or pharmaceutical composition is a topical solution or a topical ointment.

The present invention also provides use of a locked nucleic acid-modified, and phosphorothioate bond-modified oligonucleotide sequence according to the present invention for the manufacture of a medication or pharmaceutical composition for preventing or treating myopia. In a preferred embodiment, the medication or pharmaceutical composition is a topical solution or a topical ointment.

The following examples further illustrate the present invention. These examples are intended merely to be illustrative of the present invention and are not to be construed as being limiting.

EXAMPLES

Example 1. Antisense Oligonucleotides (DNA) Synthesis and Purification

Anti-sense miR-328 oligonucleotides that consist of DNA nucleotides were designed according to mature human miR-328 and human pre-miR-328 sequences. The DNA antisense oligonucleotides were synthesized using the DNA/RNA synthesizer called Dr. Oligo192 (Biolytic Lab Performance Inc.) according to manufacturer's instructions. Anti-sense oligonucleotides ranging 15mers to 30mers containing all deoxyribonucleotides were made. The products were purified by HPLC. The synthesis and purification of the antisense oligonucleotides were performed by the Genomics BioSci & Tech. Ltd. (Taiwan). The sequences of DNA 15mer-30mer are shown in Table 1.

Example 2. Antisense Oligonucleotides (LNA) Synthesis and Purification

LNA-modified, and PS bond modified antisense oligonucleotides ranged from 17 to 22 mers were designed according to mature human miR-328 sequence and gapmer principle; the modified sequences and the non-modified version are shown in Table 2. According to the design, the LNA-modified, and PS bond modified antisense sequences of 17-22 mers were synthesized and purified by Exiqon (Denmark).

Example 3. In Vitro Tests for Inhibition of miR-328 Expression by Antisense Oligonucleotides Cell Culture, Treatments, and Transfection An RPE cell line called "ARPE-19" was grown in Dulbecco's modified Eagle's medium (DMEM)/F12 medium. The cell line was grown with 1% penicillin/streptomycin and 10% heat-inactivated fetal bovine serum (FBS) at 37° C. in a humidified atmosphere of 95% air/5° J° carbon dioxide ($CO_2$). To conduct the transfection experiments, cells were seeded into a 12-well plate at a density of $1\times10^5$ cells/well. After achieving 70% confluence in a well, antisense oligonucleotides (concentrations of 30, 50 and 100 nM) were transfected with Lipofectamine 2000 (Invitrogen) according to the manufacturer's instructions. After 24 hours of incubation, cells were lysed for further studies.

Detect the Inhibition of miR-328 Expression by Antisense Oligonucleotides

Total RNA was extracted from cultured cells using Trizol according to the manufacturer's instructions. RNA purity was checked using A260/A280 readings. miR-328 was first reversed transcribed to miR-328 cDNA using the following procedure: 5 ng of RNA was reverse transcribed with miR-328 specific primer and MultiScribe reverse transcriptase kit (Applied Biosystems). To measure the miR-328 expression, quantitative real-time PCR was performed on an ABI 7500 real-time PCR machine (Applied Biosystems) with miR-328 specific probe according to manufacturer's instructions (Applied Biosystems). The inhibitory effect by antisense oligonucleotides was evaluated by measuring the level of miR-328 cDNA by quantitative real-time PCR. The expression level of miR-328 was normalized to that of a small non-coding nuclear RNA U6 as the internal control.

Results from In Vitro Tests for Inhibition of miR-328 Expression by Antisense Oligonucleotides a. DNA Anti-Sense Oligonucleotides Sixteen DNA antisense oligonucleotides, from 15 to 30 mers in length prepared according to Example 1, were examined for their inhibitory effects on the expression of miR-328 in RPE cells. The relative miR-328 expression levels are shown in FIG. 1. Only DNA16mer and DNA17mer inhibited miR-328 expression. The inhibitory effects of DNA16mer were 39%, 35% and 49% under the concentrations of 30, 50 and 100 nM. For DNA17mer, the inhibitory effects were 43%, 41% and 48% under the concentrations of 30, 50 and 100 nM. The rest of antisense oligonucleotides (15mer and 18-30mers) showed no inhibitory effect on miR-328 expression.

b. LNA-Modified Antisense Oligonucleotides

Figure 2:
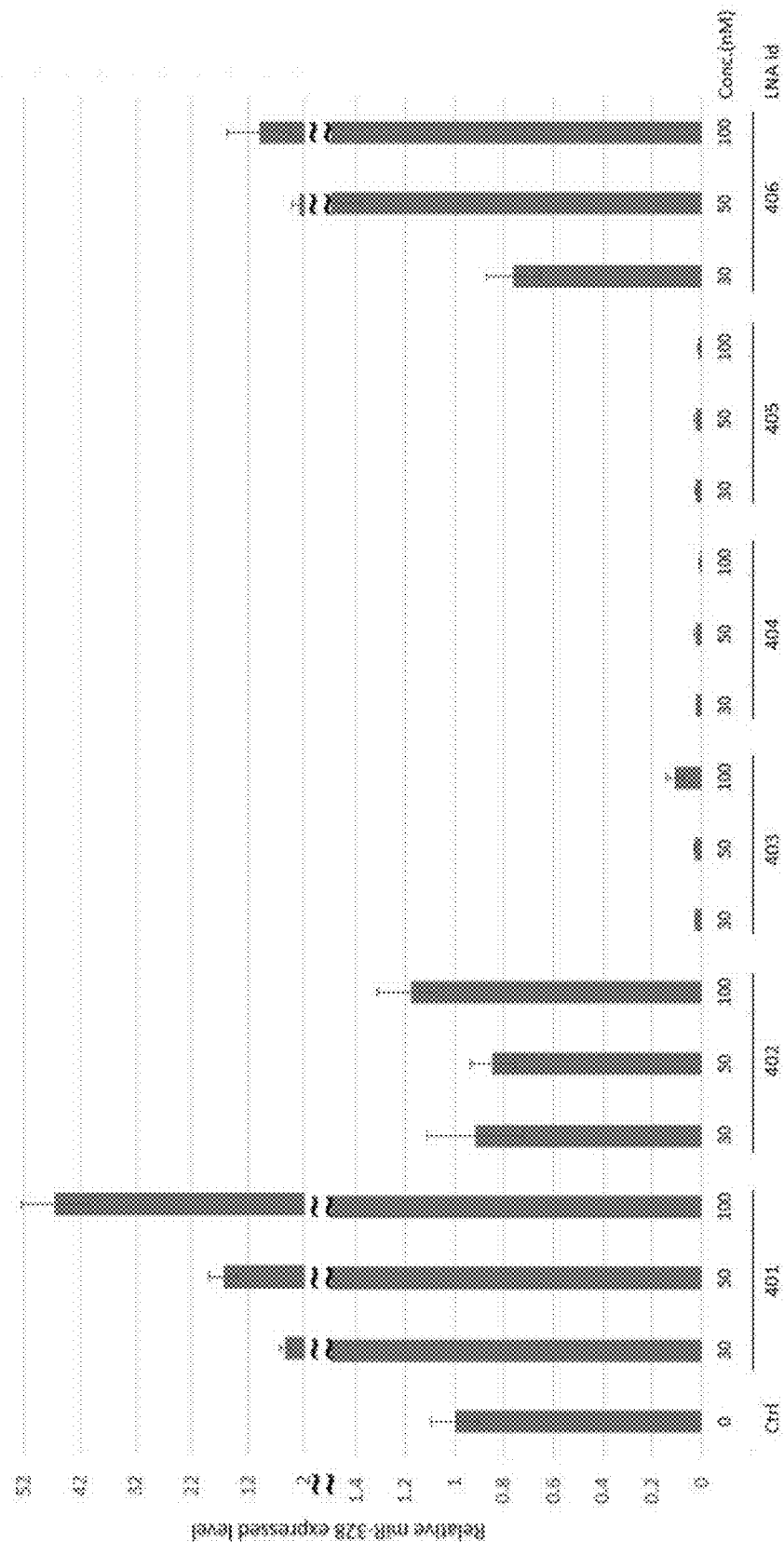
FIG. 2 shows relative miR-328 expressed levels in RPE cells after transfection with miR-328 anti-sense DNA modified by locked nucleic acids and phosphorothioated bonds (401-406) and control. Mean and standard deviation are shown (n=3).

Six LNA-modified antisense sequences, named LNA401 to LNA406, were examined for the inhibitory effect on miR-328 expression in RPE cells. The relative miR-328 expressed levels are shown in FIG. 2. Only LNA403, LNA404 and LNA405 inhibited miR-328 expression. The inhibitory effects of LNA403 were 97%, 97% and 90% under the concentrations of 30, 50 and 100 nM, respectively. LNA404 and LNA405 had the same the inhibitory effects of 98%, 98% and 99% under the concentrations of 30, 50 and 100 nM, respectively. The rest of LNA oligonucleotides showed no inhibitory effect on miR-328 expression.

Figure 3:
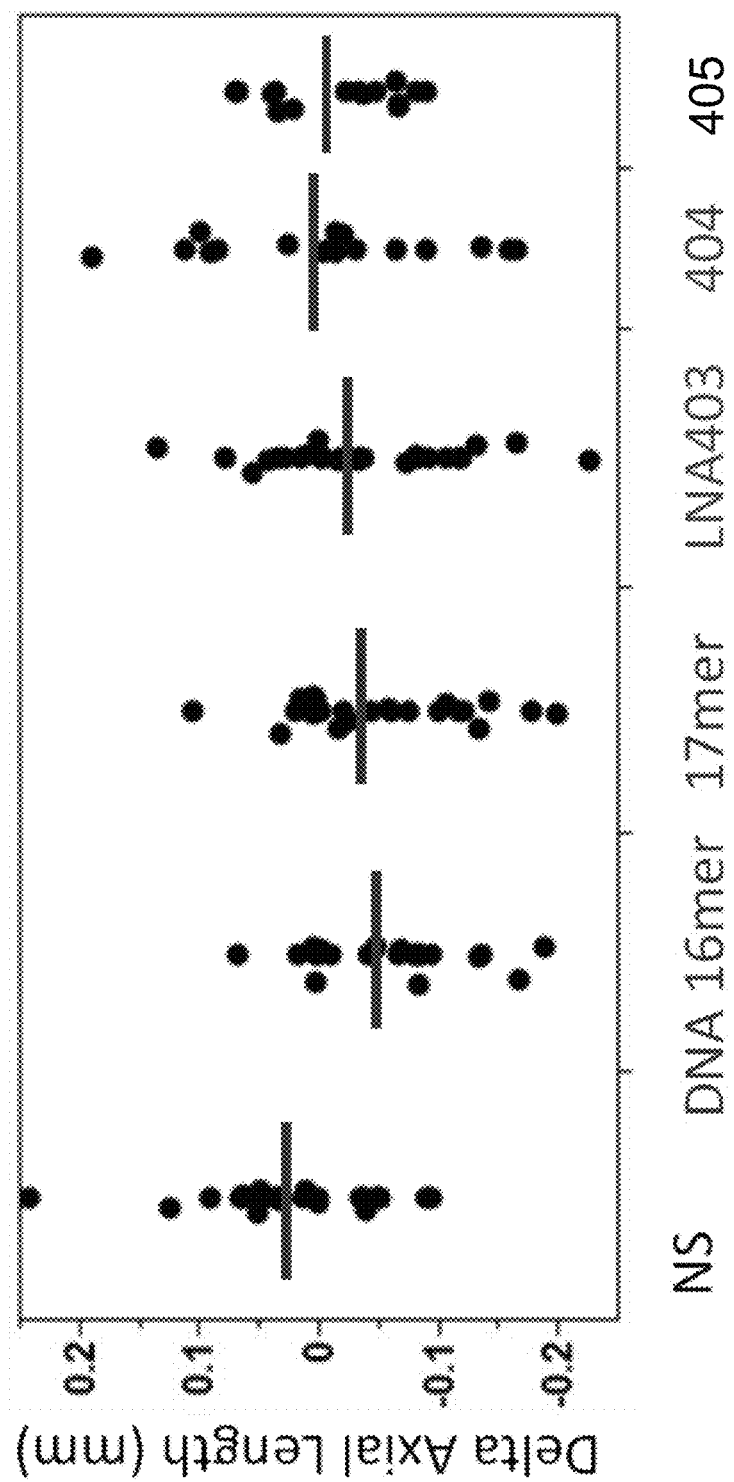
FIG. 3 shows the delta axial length of mice between right eye (myopia) and left eye in mice treated with saline control (NS), DNA 16mer, DNA 17mer, LNA 403, LNA404, and LNA 405.

Example 4. In Vivo Study to Evaluation of Efficacy of Antisense Oligonucleotides in Treating Nearsightedness Animal Model The 21 days old C57BL/6J mice were purchased from the National Laboratory Animal Center, Taiwan. All animal experiments were in compliance with the ARVO Statement for the Use of Animals in Ophthalmic and Vision Research. The procedure of myopia induction is described briefly as the following: Right eyes of the 23 days old mice were covered to induce myopia (i.e. nearsightedness) and the left eyes were uncovered. Then the right eyes of the myopia-induced mice were treated with 30 μL of saline (i.e. control group), DNA16mer, DNA17mer, LNA403, LNA404, or LNA405, at 1 μM on $30^{th}$, $37^{th}$ and $44^{th}$ day. Mice were sacrificed on $51^{st}$ day and the eyes were collected. The isolated eyes were photographed under a dissection microscope and the axial lengths were measured using imagek Myopia (nearsightedness) causes elongation of axial length, which is the major pathological change in myopia. The difference of axial length (i.e. delta axial length) between the covered right eye and the non-covered left eye of the same mouse indicates the severity of myopia. The results are summarized in Table 3 and FIG. 3. Statistical evaluation was done by using Mann-Whitney U test. Analysis with p-values<0.05 being considered significant.

TABLE 3

Delta axial length of mice treated with antisense oligonucleotides or saline

|  | Animal Number | Delta axial length, mm mean (SD) |
| --- | --- | --- |
| Saline | 26 | 0.018 (0.072) |
| DNA 16mer | 25 | −0.059 (0.061)* |
| DNA 17mer | 26 | −0.047 (0.073)* |
| LNA 403 | 27 | −0.036 (0.079)* |
| LNA 404 | 17 | −0.007 (0.100) |
| LNA 405 | 16 | −0.017 (0.054) |

*indicated significant difference with p value <0.05, when compared to Saline group DNA16mer and DNA17mer The average delta axial length in mice treated with DNA16mer and DNA17mer were statistically significantly smaller than that in control animals. DNA16mer and DNA17mer significantly reduced the delta axial length by 0.077 mm and 0.065 mm compared to control group. The results showed that DNA16mer and DNA17mer were effective in treating myopia in mice.

LNA-Modified Antisense Oligonucleotides

The average delta axial lengths in mice treated with LNA403-405 were smaller than that in control animals. LNA403 reduced the delta axial length by 0.054 mm, LNA404 reduced the delta axial length by 0.025 mm and LNA405 reduced the delta axial length by 0.035 mm, when compared to control group. However, only LNA 403 shows a statistical significance (p value<0.05). The results showed that LNA403 was effective in treating myopia in mice.

Example 5. Validation of DNA 16Mer and LNA 403

Animal Model

Figure 4:
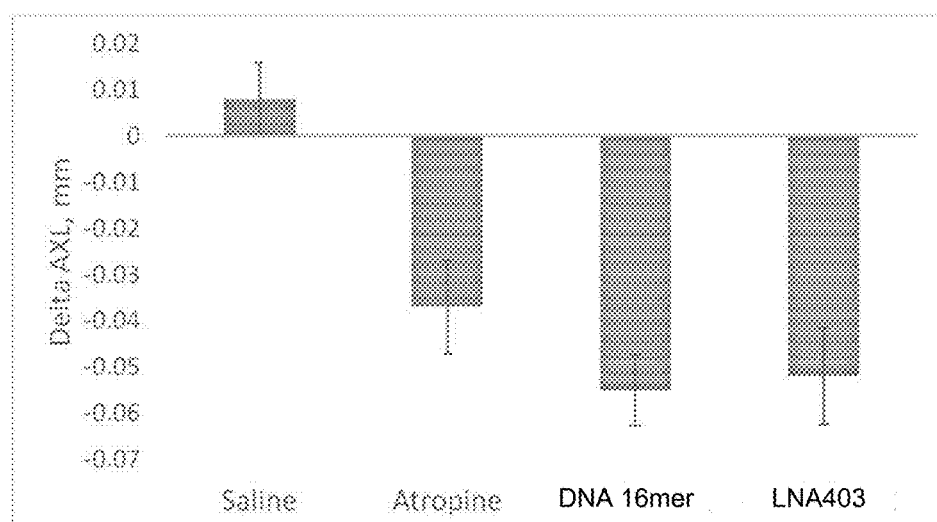
FIG. 4 shows the delta axial length of mice between right eye (myopia) and left eye in mice treated with saline control (saline), 1% atropine (atropine), DNA 16mer, and LNA 403.

The 21 days old C57BL/6J mice were purchased from the National Laboratory Animal Center, Taiwan. All animal experiments were in compliance with the ARVO Statement for the Use of Animals in Ophthalmic and Vision Research. The procedure of myopia induction is described briefly as the following: Right eyes of the 23 days old mice were covered for 4 weeks to induce myopia (i.e. nearsightedness) and the left eyes were uncovered. Then the right eyes of the myopia-induced mice were treated with 30 µL of saline (i.e. negative control group), 1% atropine (i.e. positive control group), DNA16mer or LNA403 at 1 µM on $30^{th}$, $37^{th}$ and $44^{th}$ day. Mice were sacrificed on $51^{th}$ day and the eyes were collected. The isolated eyes were photographed under a dissection microscope and the axial lengths were measured using imageJ and a proprietary software for automatic measure. Myopia (nearsightedness) causes elongation of axial length, which is the major pathological change in myopia. The difference of axial length (i.e. delta axial length) between the covered right eye and the non-covered left eye of the same mouse indicates the severity of myopia. The results are summarized in Table 4 and FIG. 4. Statistical evaluation was done by using Mann-Whitney U test. Analysis with p-values <0.05 being considered significant.

TABLE 4

Delta axial length of mice treated with atropine, antisense oligonucleotides or saline

|  | n | Mean of delta AXL | SE | p |
|---|---|---|---|---|
| Saline | 26 | 0.008 | 0.008 |  |
| 1% Atropine | 28 | −0.037 | 0.010 | <0.0001 |
| DNA 16mer | 38 | −0.055 | 0.008 | <0.0001 |
| LNA403 | 40 | −0.052 | 0.011 | 0.0024 |

AXL: axial length of eyeball

To further compare the efficacy of DNA 16mer and LNA 403 with the well-documented anti-myopia drug (atropine), we tested these three types of eyedrop. It needs to be noticed that we used 1% atropine that is 10× higher concentration than clinical concentration, and 1% atropine has been shown to be the most effective than lower concentration. Since DNA 16mer and LNA403 were dissolved in normal saline, we used normal saline as the negative control. The above data showed that both DNA 16mer and LNA403 were more effective than 1% atropine in reducing elongation of eyeball.

Example 6. Confirmation of DNA 16Mer by an Independent Third Party

We also used a CRO to confirm our results of DNA 16mer.

Animal Model

The procedure of myopia induction is: The 21 days old C57BL/6J mice were purchased from the National Laboratory Animal Center, Taiwan. All animal experiments were in compliance with the ARVO Statement for the Use of Animals in Ophthalmic and Vision Research. The procedure of myopia induction is described briefly as the following: Right eyes of the 23 days old mice were covered for 4 weeks to induce myopia and the left eyes were uncovered. Then the right eyes of the myopia-induced mice were treated with 304, of saline (i.e. negative control group), 1% atropine (i.e. positive control group), 10 nM, 100 nM, and 1 µM of DNA 16mer on $30^{th}$, $37^{th}$ and $44^{th}$ day. Mice were sacrificed on $51^{th}$ day and the eyes were collected. The isolated eyes were photographed under a dissection microscope and the axial lengths were measured using imageJ and a proprietary software for automatic measure. Myopia (nearsightedness) causes elongation of axial length, which is the major pathological change in myopia. The difference of axial length (i.e. delta axial length) between the covered right eye and the non-covered left eye of the same mouse indicates the severity of myopia.

Figure 5:
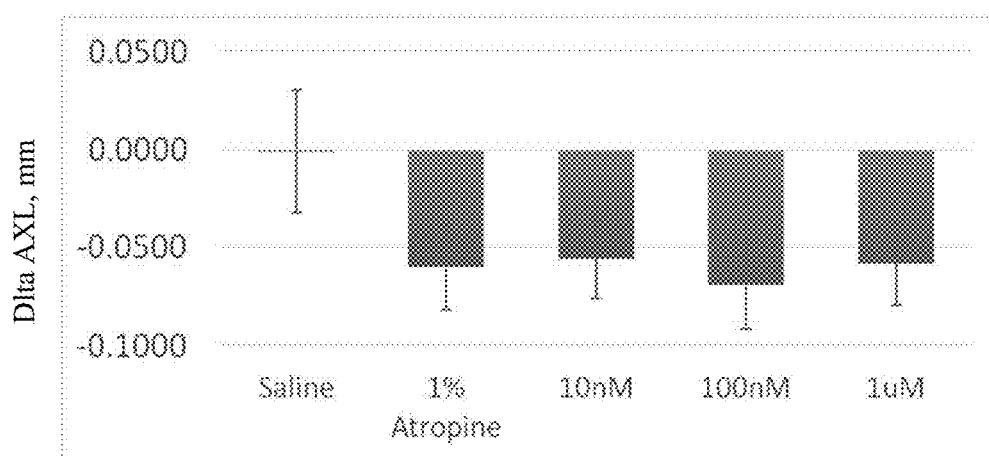
FIG. 5 shows the delta axial length of mice between right eye (myopia) and left eye in mice treated with saline control (saline), 1% atropine, 10 nM, 100 nM, and 1 µM of DNA 16mer.

The results of the CRO experiments are shown in Table 5 and FIG. 5. The $3^{rd}$ party results completely replicate our data.

TABLE 5

Delta axial length of mice treated with atropine, antisense oligonucleotides or saline

|  | n | left eye axial, mm Mean (SEM) | | right eye axial, mm Mean (SEM) | | Delta axial length Mean (SEM) | |
|---|---|---|---|---|---|---|---|
| Saline | 24 | 3.135 | (0.027) | 3.135 | (0.019) | −0.001 | (0.031) |
| 1% Atropine | 24 | 3.108 | (0.018) | 3.049 | (0.020) | −0.060 | (0.022) |
| DNA 16mer 10 nM | 24 | 3.139 | (0.013) | 3.083 | (0.021) | −0.056 | (0.020) |
| DNA 16mer 100 nM | 24 | 3.092 | (0.017) | 3.023 | (0.017) | −0.069 | (0.022) |
| DNA 16mer 1 µM | 24 | 3.110 | (0.018) | 3.052 | (0.021) | −0.058 | (0.021) |

Example 7. Confirm DNA 16Mer Effect on a $2^{nd}$ Animal

Animal Model

The procedure of myopia induction: The 3 days old pigmented rabbits were purchased from the DA-ZONG livestock farm, Taiwan. All animal experiments were in compliance with the ARVO Statement for the Use of Animals in Ophthalmic and Vision Research. On the age of 7 days, the right eye of the rabbit was covered for 8 weeks to induce myopia, and the left eye left uncovered. The axial lengths (AXL) of both eyes were measured by A-scan (Sonomed®, PACSCAN 300A, USA) once a week since day 21. We defined myopia as right eye AXL is longer than left eye AXL by 0.2 mm or longer on day 35. If a rabbit reached this defined criterion, the right eye of such a myopic rabbit was treated with 204, of saline (i.e. control group) or DNA16mer (20 µL) at 10 µM or 50 uM every other day since day 35 till day 63. The final AXL measured on day 61 was used to obtain to calculate the difference between right AXL and left AXL (i.e. delta AXL). If there is no therapeutic effect, the delta AXL will be a positive value.

Figure 6:
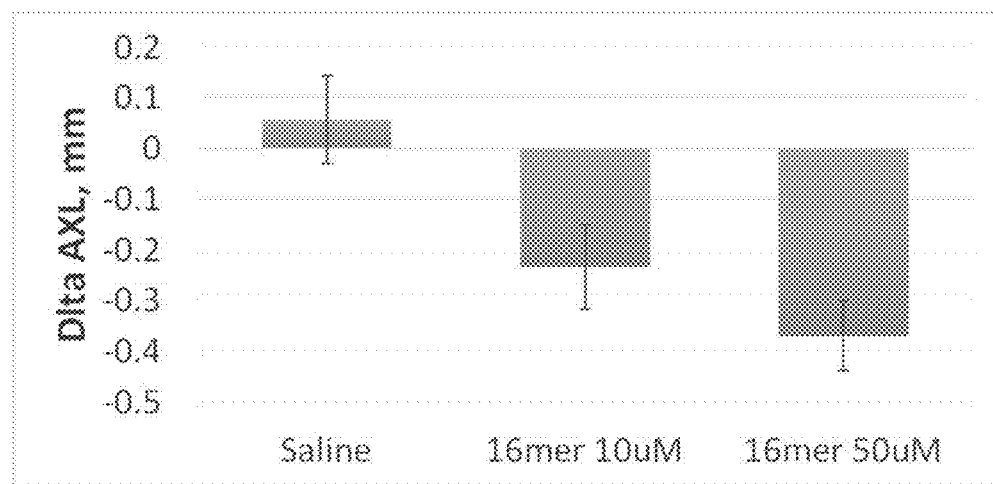
FIG. 6 shows the delta axial length of rabbit between right eye (myopia) and left eye in rabbit treated with saline control (saline), 10 µM, and 50 µM of DNA 16mer.

The results indicate a dose-dependent response for reducing AXL in myopic eyes (see Table 6 and FIG. 6).

TABLE 6

Delta axial length of rabbits treated with antisense oligonucleotides or saline

| | | Delta axial length | |
|---|---|---|---|
| | n | Mean | SEM |
| Saline | 15 | 0.051 | 0.056 |
| DNA 16mer 10 μM | 9 | −0.234 | 0.083 |
| DNA 16mer 50 μM | 4 | −0.370 | 0.068 |

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A deoxyribonucleotide sequence consisting of the sequence of SEQ ID NO: 3 or SEQ ID NO: 4.

2. The deoxyribonucleotide sequence according to claim 1, which is consisted of SEQ ID NO: 3.

3. The deoxyribonucleotide sequence according to claim 1, which is consisted of SEQ ID NO: 4.

4. A pharmaceutical composition comprising the deoxyribonucleotide sequence according to claim 1 and a pharmaceutically acceptable carrier.

5. A method for preventing or treating myopia in a subject in need thereof, comprising administering to the subject the pharmaceutical composition according to claim 4.

6. A locked nucleic acid-modified, and phosphorothioate bond-modified oligonucleotide sequence consisting of the sequence of SEQ ID NO: 21, wherein from the 5' end to the 3' end of SEQ ID NO: 21, positions 1, 2, 3, 4, 17, 18, 19 and 20 are modified by locked nucleic acid and every phosphodiester bond of SEQ ID NO: 21 is modified to a phosphorothioate bond.

7. A pharmaceutical composition comprising the locked nucleic acid-modified, and phosphorothioate bond-modified oligonucleotide sequence according to claim 6 and a pharmaceutically acceptable carrier.

8. A method for preventing or treating myopia in a subject in need thereof, comprising administering to the subject the pharmaceutical composition according to claim 6.

* * * * *

SEQUENCE LISTING

<160> NUMBER OF SEQ ID NOS: 23

<210> SEQ ID NO 1
<211> LENGTH: 22
<212> TYPE: RNA
<213> ORGANISM: Homo sapiens

<400> SEQUENCE: 1
cuggcccucu cugcccuucc gu                                               22

<210> SEQ ID NO 2
<211> LENGTH: 15
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 2
gggcagagag ggcca                                                       15

<210> SEQ ID NO 3
<211> LENGTH: 16
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 3
agggcagaga gggcca                                                      16

<210> SEQ ID NO 4
<211> LENGTH: 17
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 4
aagggcagag agggcca                                                     17

<210> SEQ ID NO 5
<211> LENGTH: 18
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 5
gaagggcaga gagggcca                                                    18

```
<210> SEQ ID NO 6
<211> LENGTH: 19
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 6
ggaagggcag agagggcca                                                    19

<210> SEQ ID NO 7
<211> LENGTH: 20
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 7
cggaagggca gagagggcca                                                   20

<210> SEQ ID NO 8
<211> LENGTH: 21
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 8
acggaagggc agagagggcc a                                                 21

<210> SEQ ID NO 9
<211> LENGTH: 22
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 9
acggaagggc agagagggcc ag                                                22

<210> SEQ ID NO 10
<211> LENGTH: 23
<212> TYPE: DNA
<213> ORGANISM: Artificial
<220> FEATURE:
<223> OTHER INFORMATION: designed anti-sense miR-328
      oligodeoxyribonucleotides according to premature human miR-328

<400> SEQUENCE: 10
acggaagggc agagagggcc agg                                               23

<210> SEQ ID NO 11
<211> LENGTH: 24
<212> TYPE: DNA
<213> ORGANISM: Artificial
<220> FEATURE:
<223> OTHER INFORMATION: designed anti-sense miR-328
      oligodeoxyribonucleotides according to premature human miR-328

<400> SEQUENCE: 11
acggaagggc agagagggcc aggg                                              24
```

```
<210> SEQ ID NO 12
<211> LENGTH: 25
<212> TYPE: DNA
<213> ORGANISM: Artificial
<220> FEATURE:
<223> OTHER INFORMATION: designed anti-sense miR-328
      oligodeoxyribonucleotides according to premature human miR-328

<400> SEQUENCE: 12
acggaagggc agagagggcc agggg                                          25

<210> SEQ ID NO 13
<211> LENGTH: 26
<212> TYPE: DNA
<213> ORGANISM: Artificial
<220> FEATURE:
<223> OTHER INFORMATION: designed anti-sense miR-328
      oligodeoxyribonucleotides according to premature human miR-328

<400> SEQUENCE: 13
acggaagggc agagagggcc aggggc                                         26

<210> SEQ ID NO 14
<211> LENGTH: 27
<212> TYPE: DNA
<213> ORGANISM: Artificial
<220> FEATURE:
<223> OTHER INFORMATION: designed anti-sense miR-328
      oligodeoxyribonucleotides according to premature human miR-328

<400> SEQUENCE: 14
acggaagggc agagagggcc aggggct                                        27

<210> SEQ ID NO 15
<211> LENGTH: 28
<212> TYPE: DNA
<213> ORGANISM: Artificial
<220> FEATURE:
<223> OTHER INFORMATION: designed anti-sense miR-328
      oligodeoxyribonucleotides according to premature human miR-328

<400> SEQUENCE: 15
acggaagggc agagagggcc aggggctg                                       28

<210> SEQ ID NO 16
<211> LENGTH: 29
<212> TYPE: DNA
<213> ORGANISM: Artificial
<220> FEATURE:
<223> OTHER INFORMATION: designed anti-sense miR-328
      oligodeoxyribonucleotides according to premature human miR-328

<400> SEQUENCE: 16
acggaagggc agagagggcc aggggctgt                                      29

<210> SEQ ID NO 17
<211> LENGTH: 30
<212> TYPE: DNA
<213> ORGANISM: Artificial
<220> FEATURE:
<223> OTHER INFORMATION: designed anti-sense miR-328
      oligodeoxyribonucleotides according to premature human miR-328

<400> SEQUENCE: 17
acggaagggc agagagggcc aggggctgta                                     30
```

```
<210> SEQ ID NO 18
<211> LENGTH: 17
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 18
aagggcagag agggcca                                                    17

<210> SEQ ID NO 19
<211> LENGTH: 18
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 19
gaagggcaga gagggcca                                                   18

<210> SEQ ID NO 20
<211> LENGTH: 19
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 20
ggaagggcag agagggcca                                                  19

<210> SEQ ID NO 21
<211> LENGTH: 20
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 21
cggaagggca gagagggcca                                                 20

<210> SEQ ID NO 22
<211> LENGTH: 21
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 22
acggaagggc agagagggcc a                                               21

<210> SEQ ID NO 23
<211> LENGTH: 22
<212> TYPE: DNA
<213> ORGANISM: Artificial
<220> FEATURE:
<223> OTHER INFORMATION: designed anti-sense miR-328
      oligodeoxyribonucleotides according to mature human miR-328

<400> SEQUENCE: 23
acggaagggc agagagggcc ag                                              22
```